United States Patent [19]

Nishimura et al.

[11] 4,029,780

[45] June 14, 1977

[54] 3-PIPERAZINYL 1,2,4-BENZOTHIADIAZINE 1,1-DIOXIDE DERIVATIVES THEIR COMPOSITIONS AND METHOD OF USE

[75] Inventors: Haruki Nishimura, Ikeda; Masanao Shimizu, Toyonaka; Naonobu Hatano, Takaishi; Katsuyoshi Nakatsuzi, Sakai; Hiroaki Kinugasa, Tsuzuki; Hiroko Kon, Kobe, all of Japan

[73] Assignee: Dainippon Pharmaceutical Co., Ltd., Osaka, Japan

[22] Filed: Oct. 28, 1975

[21] Appl. No.: 626,042

[30] Foreign Application Priority Data

Oct. 29, 1974 Japan ............................ 49-125135
Feb. 4, 1975 Japan .............................. 50-15050

[52] U.S. Cl. ............................. 424/246; 260/243 D
[51] Int. Cl.$^2$ ................ C07D 285/24; A61K 31/54
[58] Field of Search ............... 260/243 D; 424/246

[56] References Cited

UNITED STATES PATENTS

| | | | |
|---|---|---|---|
| 3,133,918 | 5/1964 | MacPhillamy et al. | 260/243 D |
| 3,163,644 | 12/1964 | de Stevens et al. | 260/243 D |
| 3,269,906 | 8/1966 | Topliss et al. | 260/243 D |
| 3,957,769 | 5/1976 | Sowinski et al. | 260/243 D |
| 3,960,854 | 6/1976 | Novello | 260/243 D |

OTHER PUBLICATIONS

Cronin et al., "J. of Med. Chemistry" vol. 11, 1968, pp. 136-138, RS-1-J5.
Sprague, "Annals: New York Academy of Sciences", 1958, vol. 71, pp. 328-343.
Yale et al., "JACS", vol. 82, 1960, pp. 2042-2043
Norrison et al., "Organic Chemistry", 1966, p. 74.

*Primary Examiner*—Donald G. Daus
*Assistant Examiner*—David E. Wheeler
*Attorney, Agent, or Firm*—Sherman & Shalloway

[57] ABSTRACT

A compound of the formula

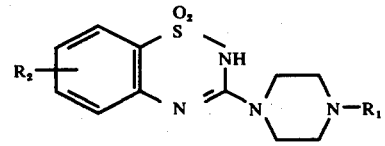

wherein $R_1$ represents a hydrogen atom or a lower alkyl group, and $R_2$ represents a hydrogen or halogen atom or a trifluoromethyl group, and its pharmaceutically acceptable salt. The compound is prepared by reacting the corresponding 1,2,4-benzothiadiazine 1,1-dioxide with a piperazine compound or alkylating 1,2,4-benzothiadiazine 1,1-dioxide whose corresponding 3-position is substituted by a piperazinyl group. The above compound has superior antihypertensive activity separated from diuretic, antidiuretic and hyperglycemic activities, and is free from side-effects.

11 Claims, No Drawings

3-PIPERAZINYL 1,2,4-BENZOTHIADIAZINE 1,1-DIOXIDE DERIVATIVES THEIR COMPOSITIONS AND METHOD OF USE

This invention relates to novel 1,2,4-benzothiadiazine 1,1-dioxide derivatives, and more particularly, to 3-(4-substituted or unsubstituted-1-piperazinyl)-2H-1,2,4-benzothiadiazine 1,1-dioxide derivatives and pharmaceutically acceptable salts thereof, a process for preparing these derivatives or salts thereof, and their use as medicines.

The invention provides novel 1,2,4-benzothiadiazine 1,1-dioxide derivatives of the following general formula

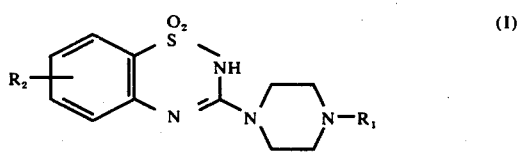

wherein $R_1$ represents a hydrogen atom or a lower alkyl group, and $R_2$ represents a hydrogen or halogen atom or a trifluoromethyl group,
and their pharmaceutically acceptable salts.

The compounds of formula (I) can exist in the form of one or both of two tautomers of formulae (Ia) and (Ib)

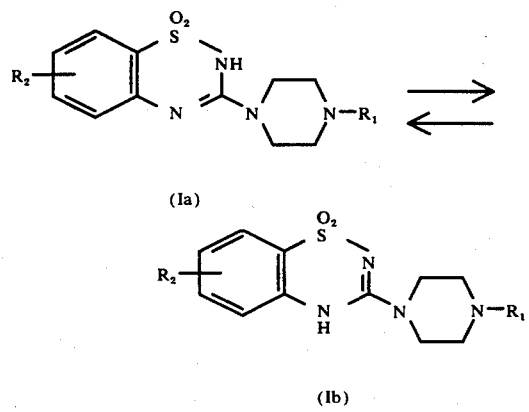

The compounds of this invention include either one or both of the tautomers, but for the convenience of description, all of the compounds will be described in the present application with regard to the form of formula (Ia), and termed accordingly.

In formula (I), the lower alkyl group is of a straight chain or branched chain, and contains up to 5 carbon atoms, preferably up to 3 carbon atoms. Examples of it are methyl, ethyl, and n- or iso-propyl, the methyl being especially suitable. The halogen atom may, for example, be chlorine or bromine. Chlorine at the 7-position is especially preferred.

Preferred compounds of formula (I) are as follows:
7-chloro-3-(4-methyl-1-piperazinyl)-2H-1,2,4-benzothiadiazine 1,1-dixoide,
3-(4-methyl-1-piperazinyl)-2H-1,2,4-benzothiadiazine 1,1-dioxide,
7-bromo-3-(4-methyl-1-piperazinyl)2H-1,2,4-benzothiadiazine 1,1-dioxide,
7-chloro-3-(1-piperazinyl)-2H-1,2,4-benzothiadiazine 1,1-dioxide, and
6-trifluoromethyl-3-(4-methyl-1-piperazinyl)-2H-1,2,4-benzothiadiazine 1,1-dioxide.

Of these, the first two are especially preferred.

The compounds of formula (I) have superior antihypertensive activity. Since the antihypertensive activity of these compounds is separated from diuretic, antidiuretic and hyperglycemic activities, they are very useful as medicines for the treatment of hypertension which are free from side-effects.

Two types of 1,2,4-benzothiadiazine 1,1-dioxide derivatives are now used for the treatment of hypertension. One type includes thiazide-type agents which are antihypertensive agents having a diuretic action, and the other is diazoxide (7-chloro-3-methyl-2H-1,2,4-benzothiadiazine 1,1-dioxide) which is an antihypertensive agent having no diuretic action. It is well known that the "thiazide" diuretic antihypertensive agents in long-term administration, often induce hypokalemia and cause a decrease in glucose tolerance which in turn induces latent diabetes or aggravates diabetes. On the other hand, diazoxide shows marked hyperglycemic effects and antidiuretic effects (i.e., sodium and water retaining effect), and is regarded as unsuitable for long-term oral administration.

A number of reports have previously been made as to 3-amino-2H-1,2,4-benzothiadiazine 1,1-dioxide and its derivatives as compounds having a 2H-1,2,4-benzothiadiazine skeleton [see, for example, U.S. Pat. No. 3,269,906; German Pat. No. 1,470,316; Farmaco Ed. Sci. 17, 974–87 (1962); ibid. 20, 647–61 (1965); J. Med. Chem. 11, 136–38 (1968); Acta Chem. Scand. 27, 2655–60 (1973); Farmaco Ed. Sci. 29. 411–23 (1974)]. Some of these compounds are reported to have antihypertensive activity. However, these reports fail to give any statement that the antihypertensive activity of these compounds is separated from their diuretic, antidiuretic and hyperglycemic activities.

For example, U.S. Pat. No. 3,269,906 states that 6-trifluoromethyl- and 6,7-dichloro-3-amino-2H-1,2,4-benzothiadiazine 1,1-dioxide are useful compounds having antihypertensive activity. It is reported however that the former has substantially the same degree of antihypertensive activity as diazoxide, but it also shows antidiuretic activity similar to that of diazoxide [Acta Chem. Scand. 27, 2655–60 (1973)]. The latter is not entirely satisfactory because of its hyperglycemic activity as will be shown by the results of our experiments to be given hereinbelow Some 1,2,4-benzothiadiazine 1,1-dioxide derivatives are known which contain a cyclic amino group at the 3-position as the compounds of formula (I). These known compounds show little or no antihypertensive activity. For example, it is reported that 3-morpholino-6-trifluoromethyl-2H-1,24-benzothiadiazine 1,1-dioxide and 6,7-dimethoxy-3-(4-methyl-1-piperazinyl)-2H-1,2,4-benzothiadiazine 1,1-dioxide show not antihypertensive activity [see Acta Chem. Scand. 27, 2655-60 (1973) and J. Med. Chem. 11, 136–38 (1968)]. On the other hand, 3-piperidino-2H-1,2,4-benzothiadiazine 1,1-dioxide is reported to exhibit slight antihypertensive activity in intravenous administration [Farmaco Ed. Sci. 17, 974–87 (1962)], but as will be shown by the results of our experiments to be given hereinbelow, this compound does not show antihypertensive activity in oral administration.

None of the 3-amino-2H-1,2,4-benzothiadiazine 1,1-dioxide and its derivatives described above have been used actually for the treatment of hypertension.

Generally, in the treatment of hypertension, antihypertensive agents must be continually administered to the patients over a long period of time and therefore, the presence of side-effects poses a serious problem in administering them as medicines. Accordingly, compounds which cause a gradual fall in blood pressure by oral administration and have little side-effects are very desirable as antihypertensive agents.

With this background in the art, we have found that compounds of formula (I) are excellent antihypertensive agents which meet all of the requirements mentioned above. Since the compounds of formula (I) cause a gradual and exact fall in blood pressure expecially in oral administration, they may be used as excellent antihypertensive agents which do not cause orthostatic hypotension.

The novel compounds of this invention, as will be shown by the experimental results to be given hereinbelow, have extremely low toxicity, and do not show diuretic and antidiuretic activity. In long-term administration, too, they do not show hyperglycemic activity nor do they cause a reduction in glucose tolerance. Thus, they are very useful pharmaceutical compounds free from the above-mentioned defects of the conventional thiazide-type diuretic antihypertensive agents or diazoxide.

According to the present invention, the compounds of formula (I) and their pharmaceutically acceptable salts can be easily prepared by a process which comprises a. reacting a compound of the formula

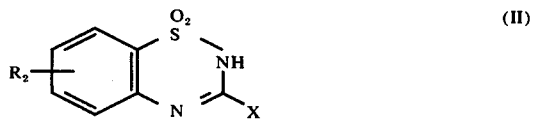

wherein X is a leaving atom or group, and $R_2$ represents a hydrogen or halogen atom or a trifluoromethyl group, with a compound of the formula

wherein $R_1$ represents a hydrogen atom or a lower alkyl group, or b. when preparing compounds of formula (I) in which $R_1$ is a lower alkyl group, alkylating a compound of the following formula

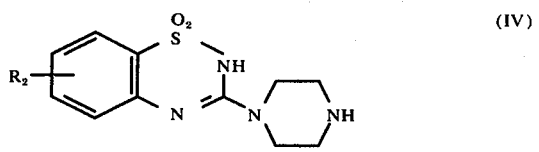

wherein $R_2$ is the same as defined above, and if desired, converting the resulting compound of formula (I) to its pharmaceutically acceptable salt.

The leaving atom or group (X) in formula (II) denotes any atom or group which can leave off in the form of HX under the reaction conditions together with the hydrogen atom bonded to the 4-position of the piperazine compound of formula (III). Examples of the leaving atom or group (X) include halogen atoms such as chlorine or bromine, an amino group, mercapto group, lower alkylthio groups, preferably those containing 1 to 4 carbon atoms, such as methylthio, ethylthio, propylthio, or butylthio, arylsulfonyloxy groups, especially benzenesulfonyloxy groups of which benzene ring is optionally substituted with a nitro group, a halogen atom, an alkyl group containing 1 to 4 carbon atoms or an alkoxy group containing 1 to 4 carbon atoms, such as benzenesulfonyloxy, p-toluenesulfonyloxy or m-nitrobenzensesulfonyloxy, and alkylsulfonyloxy groups such as methanesulfonyloxy. Of these, the halogen atoms and lower alklthio groups are especially preferred.

According to embodiment (a) of the process of this invention, the compound of formula (II) is reacted with the piperazine compound of formula (III).

The reaction of the compound of formula (II) with the piperazine compound of formula (III) can generally be carried out in the presence or absence of an inert solvent. Suitable solvents include, for example, water, alcohols such as methanol, ethanol, 2-propanol or n-butanol, ketones such as acetone or methyl ethyl ketone, hydrocarbons such as benzene, toluene, xylene or ligroin, halogenated hydrocarbons such as dichloroethane, dichlorobenzene or chloroform, ethers such as diglymer (diethylene glycol dimethyl ether), tetrahydrofuran or dioxane, acetonitrile, dimethyl sulfoxide, and dimethylformamide. These compounds can be used either alone or in combination of two or more.

The amount of the piperazine compound of formula (III) is not critical, and can be varied over a wide range according to the type of the compound of formula (II) or the reaction conditions. Generally, it is used in at least an equimolar amount, and can also be used in a large excess (preferably 1.1 to 4 moles). The compounds of formula (III) may be used in the form of hydrates or salts such as hydrochlorides or sulfates. When the piperazine compound is used in the form of its salt, the reaction is preferably carried out in the presence of a base such as an alkali metal alcoholate (e.g., sodium methylate or sodium ethylate), an alkali metal hydroxide (e.g., sodium hydroxide or potassium hydroxide), an alkali metal carbonate (e.g., sodium carbonate or potassium carbonate), an alkali metal hydrogen carbonate (e.g., sodium hydrogen carbonate or potassium hydrogen carbonate) or a tertiary amine (e.g., triethylamine or pyridine).

The reaction conditions employed in this reaction can be varied according, for example, to the type of the compounds of formula (II) and/or (III). For example, when compounds of formula (II) in which X is a halogen atom or an arylsulfonyloxy or alkylsulfonyloxy group are used as starting materials, it is preferred to perform the reaction in the presence of a base as an acid binder, such as inorganic or organic bases described above. Or it is possible to use the piperazine compound of formula (II) in excess in order to make it serve also as an acid binder. The reaction temperature is usually 0° to 150° C., preferably 20° to 70° C.

When compounds of formula (II) in which X is an amino, mercapto or lower alkylthio group are used as starting materials, the reaction is preferably performed in the absence of a solvent, although an alcohol such as ethanol, 2-propanol or n-butanol, dimethyl sulfoxide, dimethylformamide or dichlorobenzene may be used as a reaction medium. The suitable reaction temperature is 130° to 190° C.

According to embodiment (b) of the process of this invention, the compound of formula (I) in which $R_1$ is a lower alkyl group is prepared by alkylating the compound of formula (IV). The alkylation can be performed by methods known per se, for example, by treating the compound of formula (IV) with an alkylating agent. Useful alkylating agents include compounds of formula (V)

$$R_1 - Y \qquad (V)$$

wherein Y represents a reactive acid residue, and $R_1$ is the same as defined above.

Advantageously, the reactive acid residue in formula (V) is a halogen atom such as chlorine, bromine or iodine, a lower alkoxysulfonyloxy group, or a substituted or unsubstituted benzenesulfonyloxy group such as benzenesulfonyloxy or p-toluenesulfonyloxy. Examples of compounds of formula (V) are methyl iodide, dimethyl sulfate, methyl p-toluenesulfonate, and methyl benzenesulfonate.

The alkylation of the compound of formula (IV) with the compound of formula (V) can be carried out in the presence or absence of an inert solvent. The same inert solvents as illustrated above with regard to embodiment (a) can be used. The alkylating agent of formula (V) is used generally in an equimolar amount to slightly excessive amount (1.0 to 1.5 moles) based on the compound of formula (IV).

If desired, the alkylation can be carried out in the presence of a base such as an alkali metal carbonate (e.g., sodium carbonate or potassium carbonate), an alkali metal hydrogen carbonate (e.g., sodium hydrogen carbonate or potassium hydrogen carbonate) or a tertiary amine (e.g., triethylamine). The reaction temperature is usually 0° to 160° C. depending on the properties of the alkylating agent.

The alkylation of the compound of formula (IV) can be carried out by a "reductive alkylation method" by which the compound of formula (IV) is reduced in the presence of alkanals. For example, the compound of formula (IV) can be methylated by treating it with formaldehyde and formic acid as a reducing agent usually at 70° to 160° C. In this reaction, the amounts of the formaldehyde and the formic acid are not critical, and generally they are used in excess.

The starting compounds of formula (II) wherein X is a halogen atom are novel, and can be prepared by reacting the corresponding 3,4-dihydro-3-oxo-2H-1,2,4-benzothiadiazine 1,1-dioxide, which is obtained by the procedure described in J. Chem. Soc. 1950, 1760–63, with a phosphorus oxyhalide in the presence of 2,6-lutidine. Other starting compounds of formula (II) are known or easily prepared by known procedures. For example, compounds of formula (II) in which X is an amino, mercapto, lower alkylthio, arylsulfonyloxy or alkylsulfonyloxy group can be prepared by the procedures described in J. Org. Chem. 28, 2313–19 (1963), Farmaco Ed. Sci. 17, 320–30 (1962), and ibid. 16, 3–13 (1961).

The compounds of formula (I) prepared by the above processes can be isolated and purified by any conventional method such as recrystallization or reprecipitation. These compounds can be obtained in the form of a salt or a free base depending, for example, on the selection of the starting materials and the reaction conditions. When the compound of formula (I) is obtained in the form of a salt, it can be easily converted to its free base by a conventional method, for example, by treating the salt with a base such as an alkali metal hydroxide (e.g., sodium hydroxide or potassium hydroxide). On the other hand, when the compound of formula (I) is obtained as a free base, the compound may, if desired, be converted to its pharmaceutically acceptable non-toxic salts.

The compounds of formula (I) are amphoteric and their alkali metal salts and acid addition salts can therefore be prepared by a conventional method. For example, the alkali metal salts can be obtained by dissolving the compounds of formula (I) in an aqueous or lower alcoholic (e.g., methanol or ethanol) solution containing a stoichiometric amount of an alkali metal hydroxide (e.g., sodium hydroxide or potassium hydroxide) or an alkali metal alcoholate (e.g., sodium methylate), and evaporating the solvent. The acid addition salts can be obtained by reacting the compounds of formula (I) with a stoichiometric amount of a pharmaceutically acceptable inorganic or organic acid, such as hydrochloric acid, hydrobromic acid, hydriodic acid, sulfuric acid, nitric acid, phosphoric acid, acetic acid, citric acid, maleic acid, fumaric acid, succinic acid, lactic acid, malic acid, tartaric acid, benzoic acid or methanesulfonic acid. The salt formation can be carried out in aqueous or non-aqueous media such as ethanol.

The compounds of formula (I) and the salts thereof in accordance with this invention have excellent antihypertensive activity. The pharmacological properties of some of typical compounds of formula (I) are demonstrated by the following experiments.

The compounds tested are as follows:
(The compounds of this invention)
  Compound A:
   7-Chloro-3-(4-methyl-1-piperazinyl)-2H-1,2,4-benzothiadiazine 1,1-dioxide
  Compound B:
   3-(4-Methyl-1-piperazinyl)-2H-1,2,4-benzothiadiazine 1,1-dioxide
(Reference compounds)
  Compound 1:
   6,7-Dimethoxy-3-(4-methyl-1-piperazinyl)-2H-1,2,4-benzothiadiazine 1,1-dioxide [disclosed in J. Med. Chem. 11, 136–38 (1968)]
  Compound 2:
   3-Piperidino-2H-1,2,4-benzothiadiazine 1,1-dioxide [disclosed in Farmaco Ed. Sci. 17, 974-87 (1962)]
  Compound 3:
   Diazoxide
  Compound 4:
   Hydrochlorothiazide
  Compound 5:
   6,7-Dichloro-3-imino-3,4-dihydro-1,2,4-benzothiadiazine 1,1-dioxide [disclosed in U.S. Pat. No. 3,269,906 and Farmaco Ed. Sci. 17, 974–87 (1962)]

1. Antihypertensive activity

Spontaneously hypertensive male rats [SHR, Jap. Circ. J. 27, 282–93 (1963)] being 18–23 weeks of age and having systolic blood pressure levels of 170–190 mmHg were used. The test compounds were each suspended in a 0.5% aqueous tragacanth solution and administered orally in a dose of 10 mg/kg/day by stomach tube to SHR once a day for 10 successive days. The blood pressure of conscious SHR was measured prior to dosing and 5 hours after administration. It was also measured once daily over a period of 7 days after the end of the treatment period. The measurement of the blood pressure was made by a plethysmographtail method [Jap. Circ. J. 27, 282–93 (1963)]. The results are summarized in Table I.

Table I

| Test compound | Number of rats | Blood pressure (mm Hg) after the period indicated (days) | | | | | | | | | | | |
|---|---|---|---|---|---|---|---|---|---|---|---|---|---|
| | | $0^{a)}$ | | 2 | | 4 | | 6 | | 8 | | 10 | 14 |
| | | $0^{b)}$ | 5 | 0 | 5 | 0 | 5 | 0 | 5 | 0 | 5 | $0^{c)}$ | $0^{d)}$ |
| A | 5 | 172 ±5 | 172 ±4 | 167 ±3 | 155 ±7 | 158 ±6 | 151 ±7 | 144 ±4 | 131 ±6 | 143 ±5 | 135 ±6 | 139 ±9 | 165 ±5 |
| B | 5 | 169 ±2 | 167 ±2 | 167 ±3 | 161 ±3 | 159 ±2 | 154 ±2 | 160 ±2 | 144 ±8 | 149 ±3 | 136 ±5 | 146 ±4 | 166 ±3 |
| 1 | 5 | 189 ±2 | 188 ±2 | 187 ±3 | 186 ±4 | 185 ±3 | 184 ±3 | 187 ±3 | 184 ±3 | 189 ±2 | 187 ±3 | 187 ±3 | 188 ±3 |
| 2 | 5 | 187 ±5 | 180 ±4 | 186 ±4 | 181 ±4 | 182 ±5 | 183 ±5 | 186 ±6 | 186 ±5 | 186 ±4 | 183 ±4 | 184 ±4 | 182 ±6 |
| 3 | 5 | 173 ±4 | 155 ±2 | 166 ±5 | 146 ±7 | 159 ±7 | 151 ±3 | 150 ±5 | 143 ±5 | 153 ±5 | 137 ±3 | 144 ±6 | 175 ±7 |
| 4 | 5 | 172 ±2 | 168 ±6 | 163 ±2 | 152 ±2 | 158 ±5 | 150 ±5 | 151 ±5 | 138 ±8 | 152 ±1 | 140 ±7 | 153 ±6 | 165 ±4 |
| Control$^{e)}$ | 5 | 177 ±3 | 173 ±3 | 172 ±5 | 174 ±2 | 171 ±2 | 169 ±3 | 172 ±3 | 171 ±4 | 176 ±3 | 171 ±4 | 174 ±3 | 174 ±4 |

$^{a)}$the beginning of the treatment.
$^{b)}$"0": prior to dosing "5": 5hours after administration.
$^{c)}$24 hours after the final treatment.
$^{d)}$120 hours after the final treatment.
$^{e)}$The control group was given the 0.5% tragacanth solution alone.
The values in the table are ± standard error.

As shown in Table I, the compounds of this invention at a dose of 10 mg/kg/day caused a sustained fall in blood pressure without marked daily fluctuations. The antihypertensive effect of these compounds was found to be as potent as those of diazoxide and hydrochlorothiazide at the same does in SHR. The blood pressure began to drop in 3 to 5 days after the beginning of the administration of the present compounds and showed a maximum fall of 30 to 40 mmHg. However, compounds 1 and 2 did not cause any significant fall in blood pressure at the same dose.

Furthermore, the present compounds at a dose of 30 mg/kg/day p.o. exhibited a significant antihypertensive effect both in renal hypertensive rats [prepared by the procedure described in Can. Med. Assoc. J. 49, 88–92 (1943)] and in DOC hypertensive rats [prepared by the procedure described in Am. J. Physiol. 225, 1513 (1973)].

2. Effect on urine volume and electrolyte excretion

Male Wistar rats weighing 220 to 260 g were used. Each test compound was suspended in a solution of tragacanth dissolved in a concentration of 0.5% in a 0.9% saline solution so that the volume of the resulting suspension to be administered would be always 25 ml/Kg. The test compounds were administered orally by the stomach tube to the animals at the prescribed doses. The animals were then placed in a metabolic cage and the urine was collected over a period of 5 hours. The total amount of sodium, potassium and chloride excreted was determined by Auto-Analyzer, made by Technicon Instruments Corporation. The results are summarized in Table II.

Table II

| Test compound | No. of rats | Dose (mg/kg) | Urine volume (ml) | $Na^+$ (mEq) | $K^+$ (mEq) | $Na^+/K^+$ | $Cl^-$ (mEq) |
|---|---|---|---|---|---|---|---|
| A | 5 | 100 | 3.58 ±0.60 | 0.78 ±0.12 | 0.40 ±0.04 | 1.93 ±0.24 | 0.90 ±0.12 |
| B | 5 | 100 | 3.06 ±0.29 | 0.64 ±0.08 | 0.48 ±0.05 | 1.34 ±0.10 | 0.89 ±0.07 |
| 3 | 5 | 100 | 1.35 ±0.10 | 0.17 ±0.04 | 0.37 ±0.05 | 0.51 ±0.13 | 0.20 ±0.04 |
| 4 | 5 | 1.0 | 6.07 ±0.57 | 1.14 ±0.06 | 0.51 ±0.04 | 2.28 ±0.08 | 1.38 ±0.06 |
| Control* | 39 | — | 3.55 ±0.17 | 0.71 ±0.04 | 0.54 ±0.03 | 1.32 ±0.04 | 0.93 ±0.04 |

*The control group was given only the 0.5% tragacanth solution at a dose of 25 ml/kg.
The values in the table are means ± standard error.

As shown in Table II, Compound B caused no significant change in the urine volume and electrolyte excretion following a dose of 100 mg/kg. On the other hand, at the same dose as that of Compound B, Compound A caused some increase in $Na^+/K^+$ but no significant change in urine volume and electrolyte excretion. The results indicate that Compound A had substantially no effect on the electrolyte excretion.

As for the reference compound, the oral dose of 100 mg/kg of diazoxide remarkably reduced the urine volume and the sodium and potassium excretion. In contrast to the antidiuretic effect of diazoxide, at a dose of only 1 mg/kg, hydrochlorothiazide caused a marked increase in urine volume, sodium excretion and $Na^+/K^+$.

3. Effect on blood glucose a. Male Wistar rats weighing 190–210 g were used. Each test compound was suspended in a concentration of 150 mg/ml in a 0.5% aqueous tragacanth solution and orally administered at a dose of 300 mg/kg by the stomach tube. The blood samples were taken prior to dosing and 1, 3, 6 and 10 hours after the administration from the retroorbital venous plexus, and the plasma glucose levels were determined by the O.H. Lowry method [J. Biol. Chem. 239, 18 (1964)].

b. Male Wistar rats weighing 260–285 g were used. Each test compound was dissolved in a 1 N aqueous sodium hydroxide solution and diluted with 1 N hydrochloric acid to give a solution in the pH range of 10.7–11.1 and a concentration of 75 mg/ml. 4 ml/kg of the above solution of each test compound was intraperitoneally administered to each animal. The blood samples were taken prior to dosing and 1, 3 and 6 hours after the administration and the plasma glucose levels were determined in a similar manner to that described in (a).

The results of these two experiments (a) and (b) are summarized in Tables III and IV respectively.

Table III

| Test compound | Number of rats | Blood glucose (mg/dl) after the period indicated (hr) | | | | |
|---|---|---|---|---|---|---|
| | | 0 | 1 | 3 | 6 | 10 |
| A | 8 | 105 ±1 | 105 ±1 | 107 ±1 | 103 ±1 | 110 ±2 |
| B | 8 | 106 ±1 | 107 ±1 | 109 ±2 | 104 ±2 | 110 ±2 |
| 3 | 8 | 111 ±2 | 126 ±2 | 125 ±3 | 146 ±4 | 148 ±8 |
| 4 | 8 | 104 ±1 | 114 ±2 | 111 ±2 | 112 ±2 | 113 ±2 |
| 5 | 8 | 101 ±2 | 105 ±2 | 132 ±4 | 133 ±4 | 132 ±5 |
| Control* | 10 | 107 ±2 | 115 ±2 | 110 ±2 | 116 ±2 | 107 ±3 |

*The control group was given only the 0.5% tragacanth solution at a dose of 2 ml/kg.

Table IV

| Test Compound | Number of rats | Blood glucose (mg/dl) after the period indicated (hr) | | | |
|---|---|---|---|---|---|
| | | 0 | 1 | 3 | 6 |
| A | 6 | 94 ±1 | 102 ±2 | 103 ±2 | 111 ±3 |
| B | 6 | 100 ±2 | 111 ±2 | 115 ±2 | 125 ±3 |
| 3 | 6 | 100 ±3 | 361 ±7 | 599 ±16 | 675 ±28 |
| 4 | 6 | 100 ±2 | 257 ±10 | 220 ±15 | 144 ±16 |
| 5 | 6 | 104 ±2 | 323 ±10 | 412 ±24 | 310 ±27 |
| Control* | 6 | 97 ±1 | 100 ±1 | 99 ±1 | 103 ±1 |

*The control group was given only the aqueous alkaline solution of pH 10.7 – 11.1 at a dose of 4 ml/kg.

The values in Tables III and IV are means ± standard error.

At the doses of 300 mg/kg p.o. and 300 mg/kg i.p., Compound A and B had substantially no effect on the blood glucose level in rats. On the other hand, diazoxide and Compound 5 at the same doses caused a marked increase in blood glucose. The intrapertioneal dose of 300 mg/kg of hydrochlorothiazide also caused a significant and considerable increase.

4. Glucose tolerance test

Spontaneously hypertensive rats weighing 360 to 400 g were used. Each of the test compounds was suspended in a 0.5% aqueous tragacanth solution, and orally administered to the animals at a dose of 300 mg/kg once a day for 22 consecutive days. The control group was given only the 0.5% aqueous tragacanth solution. After the final administration, the animals were caused to fast for 20 hours, and subjected to a glucose tolerance test by an oral application of 1.25 g/kg of glucose.

As a result, the group administered with Compound A, after glucose application, showed the same glucose tolerance pattern as the control group, and no abnormality was observed in glucose tolerance. On the other hand, the groups administered with diazoxide and hydrochlorothiazide showed significantly high blood glucose levels after the application of glucose as compared with the control group, and abnormality in glucose tolerance was observed in these groups.

5. Toxicity

Male and female JCL-ICR strain mice, weighing 20–30 g (each group: 8 mice), and male and female JCL-SD strain rats, weighing 150–250 g (each group: 8 rats) were used. After administering Compound A, the animals were observed for 7 days and then the $LD_{50}$ was calculated by Litchfield-Wilcoxon method. The results are shown in the following Table V.

Table V

| Animal | Route | Sex | $LD_{50}$ (mg/kg) |
|---|---|---|---|
| Rats (JCL-SD) | p.o.* | Male | > 5000 |
| | | Female | > 5000 |
| | s.c.** | Male | > 1000 |
| | | Female | > 1000 |
| | i.v.** | Male | 551.0 (626.5 – 484.6) |
| | | Female | 740.1 (869.9 – 629.7) |
| Mice (JCL-ICR) | p.o.* | Male | > 5000 |
| | | Female | > 5000 |
| | s.c.** | Male | > 2412 |
| | | Female | > 2412 |
| | i.v.** | Male | 266.8 (327.8 – 217.2) |
| | | Female | 241.5 (287.2 – 203.1) |

Figures in parentheses represent 95% confidence limits.
*Compound A was suspended in 0.5% aqueous tragacanth solution.
**Compound A was dissolved in water containing stoichiometric amount of sodium hydroxide.

Thus, the compounds of this invention have excellent antihypertensive effect and quite low toxicity, and may be used as antihypertensive agents for the treatment of hypertension such as essential hypertension, renal hypertension, or malignant hypertension. The compounds may be administered through an oral or parenteral route, but preferably through oral route.

The clinical dosage of the compounds of this invention depends, for example, on the body weight, age and conditions of the patients, and the route of administration chosen. Usually they are administered in a dose of 1 to 10 mg/kg/day through oral route. The total dosage may be administered once a day or in smaller portions two, three or four times daily.

The compounds of this invention may be used in the form of pharmaceutical preparations which contain the active ingredient in admixture with an inorganic or organic, solid or liquid pharmaceutically acceptable carrier which is conventional in the field of pharmacy and suitable for enteral or parenteral administration. The pharmaceutically acceptable carriers are substances which are unreactive with the present compounds, and may, for instance, be water, gelatin, lactose, starch, cellulose (preferably microcrystalline cellulose), sodium carboxymethyl cellulose, calcium carboxymethyl cellulose and methyl cellulose, hydroxypropyl cellulose, polyvinylpyrrolidone, sorbitol, light anhydrous silicic acid, magnesium stearate, talc, vegetable fats or oils, hardened oil, benzyl alcohol, gums, propylene glycol or polyalkylene glycols. The pharmaceutical preparations may, for example, be in a solid form such as tablets, capsules, granules, powders or suppositories or in a liquid form such as solution, suspension or emulsion. They may further contain other therapeutically valuable substances. The preparations are made by conventional methods.

The preparation of the compounds of the present invention and their compositions are illustrated by the following examples, which are not to be considered as limiting the scope of the invention in any way.

EXAMPLE 1

7-Chloro-3-(4-methyl-1-piperazinyl)-2H-1,2,4-benzothiadiazine 1,1-dioxide

A mixture of 3.2 g of 7-chloro-3-methylthio-2H-1,2,4-benzothiadiazine 1,1-dioxide and 1.1 g of 1- methylpiperazine is heated with stirring in an oil bath at 140° C. for 2 hours. After cooling, the resultant solid is recrystallized from a mixture of dimethylformamide and water to give 3.1 g of the desired product, m.p. above 300° C.

Analysis - Calcd. for $C_{12}H_{15}ClN_4O_2S$: C, 45.78; H, 4.80; Cl, 11.26; N, 17.80; S, 10.18. Found: C, 45.55; H, 4.70; Cl, 11.38; N, 17.59; S, 10.08.

IR $\nu$max KBr cm$^{-1}$: 3340 (NH); 1615, 1574 (N=C—NH); 1277, 1134 (SO$_2$).

EXAMPLE 2

7-Chloro-3-(4-methyl-1-piperazinyl)-2H-1,2,4-benzothiadiazine 1,1-dioxide

To a stirred suspension of 10.0 g of 3,7-dichloro-2H-1,2,4benzothiadiazine 1,1-dioxide in 100 ml of water is added 8.0 g of 1-methylpiperazine, while the mixture is cooled in an ice bath. After the addition, the mixture is stirred at 60° C for 1 hour. The crystalline precipitate collected is recrystallized from a mixture of dimethylformamide and water to give 11.0 g of the desired product, m.p. above 300° C.

EXAMPLE 3

3-(4-Methyl-1-piperazinyl)-2H-1,2,4-benzothiadiazine 1,1-dioxide

To a stirred suspension of 10.7 g of 3-chloro-2H-1,2,4-benzothiadiazine 1,1-dioxide in 100 ml of methanol is added 9.9 g of 1-methylpiperazine and the mixture is heated under reflux for 2 hours. After cooling, the crystalline precipitate is collected by suction filtration and recrystallized from a mixture of dimethylformamide and water to give 10.0 g of the desired product, m.p. 265°–267° C.

Analysis - Calcd. for $C_{12}H_{16}N_4O_2S$: C, 51.42; H, 5.75; N, 19.99; S, 11.42. Found: C, 51.21; H, 5.79; N, 19.97; S, 11.34.

IR $\nu$max KBr cm$^{-1}$: 3290 (NH); 1613, 1578 (N=C—NH); 1260, 1152 (SO$_2$).

EXAMPLE 4

7-Chloro-3-(4-methyl-1-piperazinyl)-2H-1,2,4-benzothiadiazine 1,1-dioxide

A mixture of 3.0 g of 3-amino-7-chloro-2H-1,2,4-benzothiadiazine 1,1-dioxide and 2.5 g. of 1-methylpiperazine is heated at 185° C in a sealed tube for 8 hours. After removal of the remaining 1-methylpiperazine by distillation under reduced pressure, the residual solid is recrystallized from a mixture of dimethylformamide and water to give 2.8 g of the desired product, m.p. above 300° C.

EXAMPLE 5

3-(4-Methyl-1-piperazinyl)-2H-1,2,4-benzothiadiazine 1,1-dioxide

To a stirred suspension of 1.0 g of 3-(m-nitrobenzenesulfonyloxy)-2H-1,2,4-benzothiadiazine 1,1-dioxide in 10 ml of acetone is added dropwise 0.53 g of 1-methylpiperazine, while the mixture is cooled in an ice bath. After the addition, the mixture is stirred at room temperature for 1 hour. After removal of acetone by distillation under reduced pressure, 30 ml of water is added to the residue. The crystalline precipitate is collected by suction filtration and treated with 2 ml of a 10% aqueous sodium hydroxide solution. After removal of the insoluble materials by suction filtration, the filtrate is adjusted to a pH 8.0 with dilute hydrochloric acid. The crystalline precipitate is collected by suction filtration and recrystallized from a mixture of dimethylformamide and water to give 0.2 g of the desired product, m.p. 265°–267° C.

EXAMPLE 6

7-Chloro-3-(1-piperazinyl)-2H-1,2,4-benzothiadiazine 1,1-dioxide

To a stirred solution of 3.4 g of anhydrous piperazine in 25 ml of methanol is added 5.0 g of 3,7-dichloro-2H-1,2,4-benzothiadiazine 1,1-dioxide, while the mixture is cooled in an ice bath. After the addition, the mixture is stirred at room temperature for 3 hours. The crystalline precipitate is collected by suction filtration and treated with a mixture of 2 ml of concentrated hydrochloric acid and 40 ml of water. After removal of the insoluble materials by suction filtration, the filtrate is adjusted to a pH 8.0 with a dilute aqueous sodium hydroxide solution to give 3.9 g of the desired product, m.p. 292°–295° C. (decomposition).

Analysis - Calcd. for $C_{11}H_{13}ClN_4O_2S$: C, 43.93; H, 4.36; Cl, 11.79; N, 18.63; S, 10.66. Found: C, 43.87; H, 4.34; Cl, 11.81; N, 18.44; S, 10.73.

IR $\nu$max KBr cm$^{-1}$: 3300 (NH); 1607, 1570 (N=C—NH); 1246, 1125 (SO$_2$).

EXAMPLE 7

7-Chloro-3-(4-methyl-1-piperazinyl)-2H-1,2,4-benzothiadiazine 1,1-dioxide

A solution of 2.5 g of 7-chloro-3-(1H-2H,-1,2,4-benzothiadiazine 1,1-dioxide in 12 ml of 37% formalin and 15 ml of 85% formic acid is refluxed for 3 hours. The reaction mixture is concentrated under reduced pressure. The residual solid is dissolved in 1 ml of concentrated hydrochloric acid and 30 ml of water. The resultant solution is adjusted to a pH 8.0 with a dilute aqueous sodium hydroxide solution. The crystalline precipitate is collected by suction filtration and recrystallized from a mixture of dimethylformamide and water to give 2.1 g of the desired product, m.p. above 300° C.

EXAMPLE 8

7-Chloro-3-(4-methyl-1-piperazinyl)-2H-1,2,4-benzothiadiazine 1,1-dioxide

To a solution of 1.0 g of 7-chloro-3-(1-piperazinyl)-2H-1,2,4-benzothiadiazine 1,1-dioxide in 15 ml of dimethylformamide is added dropwise at 0° C. 0.56 g of 93% methyl iodide, in the presence of 0.7 g of anhydrous sodium carbonate. The mixture is stirred for 2 hours, while the temperature is kept at 0° C. After removal of dimethylformamide by distillation under reduced pressure, the resulting residue is triturated with 10 ml of water to precipitate the crystals. The collected precipitate is recrystallized from a mixture of dimethylformamide and water to give 0.4 g of the desired product, m.p. above 300° C.

EXAMPLE 9

The following compounds are prepared in substantially the same manner as in Examples 1–8.

7-Bromo-3-(4-methyl-1-piperazinyl)-2H-1,2,4-benzothiadiazine 1,1-dioxide, m.p. above 300° C.

Analysis - Calcd. for $C_{12}H_{15}BrN_4O_2S$: C, 40.12; H, 4.21; Br, 22.24; N, 15,60; S, 8.93. Found: C, 39.97; H, 4.09; Br, 22.33; N, 15.67; S, 8.80.

IR νmax KBr cm⁻¹: 3320 (NH); 1608, 1570 (N=C—NH); 1270, 1133 (SO$_2$).

6-Trifluoromethyl-3-(4-methyl-1-piperazinyl)-2H-1,2,4-benzothiadiazine 1,1-dioxide, m.p. above 300° C.

Analysis -Calcd. for $C_{13}H_{15}F_3N_4O_2S$: C, 44.82; H, 4.34; F, 16.36; N, 16.08; S, 9.21. Found: C, 44.79; H, 4.30; F, 16.15; N, 16.26; S, 9.51.

IR νmax KBr cm⁻¹: 3325 (NH); 1620, 1585 (N=C—NH); 1282, 1129 (SO$_2$).

EXAMPLE 10

7-Chloro-3-(4-methyl-1-piperazinyl)-2H-1,2,4-benzothiadiazine 1,1-dioxide hydrochloride To a suspension of 3.0 g of 7-chloro-3-(4-methyl-1-piperazinyl)-2H-1,2,4-benzothiadiazine 1,1-dioxide in 12 ml of water is added dropwise 1.5 ml of concentrated hydrochloric acid. The mixture is heated on a stream bath until it becomes a clear solution, which precipitates crystals on cooling. There is obtained 3.1 g of the desired product, m.p. 277°–281° C (decomposition).

The following compounds are prepared in substantially the same manner as in above Example:

7-Chloro-3-(4-methyl-1-piperazinyl)-2H-1,2,4-benzothiadiazine 1,1-dioxide hemisulfate, m.p. 227°–229° C.

7-Chloro-3-(4-methyl-1-piperazinyl)-2H-1,2,4-benzothiadiazine 1,1-dioxide tartrate, m.p. 234°–236° C. (decomposition). 3-(4-Methyl-1-piperazinyl)-2H-1,2,4-benzothiadiazine 1,1-dioxide hydrochloride, m.p. 272°–276° C. (decomposition).

EXAMPLE 11

Sodium salt of 7-chloro-3-(4-methyl-1-piperazinyl)-2H-1,2,4-benzothiadiazine 1,1-dioxide 7-Chloro-3-(4-methyl-1-piperazinyl)-2H-1,2,4-benzothiadiazine 1,1-dioxide (3.15 g) is dissolved in a solution of sodium methylate prepared by adding 0.23 g of sodium metal to 30 ml of anhydrous methanol. The resulting solution is evaporated to dryness under reduced pressure to give the desired product as a hygroscopic powder, m.p. 210°–220° C.

The starting materials used in the above Examples are prepared as follows:

REFERENCE EXAMPLE 3,7-Dichloro-2H-1,2,4-benzothiadiazine 1,1-dioxide

To a stirred suspension of 8.0 g of 7-chloro-3,4-dihydro-3-oxo-2H-1,2,4-benzothiadiazine 1,1-dioxide in 80 g of phosphorus oxychloride is added dropwise 7.4 g of 2,6-lutidine, while the mixture is cooled in an ice bath. After the addition, the mixture is heated under reflux for 12 hours and concentrated under reduced pressure. To the residue is added 400 ml of ice water and the resulting mixture is stirred for 30 minutes. The crystalline precipitate is collected by suction filtration, washed with water and then with 2-propanol, and recrystallized from 2-propanol to afford the desired product, m.p. 242°–244° C.

The following compounds are prepared in substantially the same manner as in above reference example:

3-Chloro-2H-1,2,4-benzothiadiazine 1,1-dioxide, m.p. 238°–239° C.

7-Bromo-3-chloro-2H-1,2,4-benzothiadiazine 1,1-dioxide, m.p. 269°–271° C.

3-Chloro-6-trifluoromethyl-2H-1,2,4-benzothiadiazine 1,1-dioxide, m.p. 295°–300° C.

EXAMPLE 12

|  | per 1000 tablets |
|---|---|
| 7-Chloro-3-(4-methyl-1-piperazinyl)-2H-1,2,4-benzothiadiazine 1,1-dioxide | 25 g |
| Starch | 31 g |
| Lactose | 20 g |
| Microcrystalline cellulose | 20 g |
| Hydroxypropyl cellulose | 2 g |
| Magnesium stearate | 2 g |

The above components are blended, granulated and made into tablets by a conventional method. 1,000 tablets each weighing 100 mg are formed.

EXAMPLE 13

|  | per 1,000 capsules |
|---|---|
| 7-Chloro-3-(4-methyl-1-piperazinyl)-2H-1,2,4-benzothiadiazine 1,1-dioxide | 50 g |
| Starch | 46 g |
| Hydroxypropyl cellulose | 2 g |
| Magnesium stearate | 2 g |

The above components are blended, granulated and filled into 1,000 capsules by a conventional method.

EXAMPLE 14

| 7-Chloro-3-(4-methyl-1-piperazinyl)-2H-1,2,4-benzothiadiazine 1,1-dioxide | 10 g |
|---|---|
| Starch | 89 g |
| Light anhydrous silicic acid | 1 g |

The above components are blended and made into powder by a conventional method.

EXAMPLE 15

The same procedures as in Examples 12, 13 and 14 are repeated except that 3-(4-methyl-1-piperazinyl)-2H-1,2,4-benzothiadiazine 1,1-dioxide is used instead of 7-chloro-3-(4-methyl-1-piperazinyl)-2H-1,2,4-benzothiadiazine 1,1-dioxide. Thus, tablets, capsules and powders are prepared respectively.

What we claim is:

1. A compound of the formula

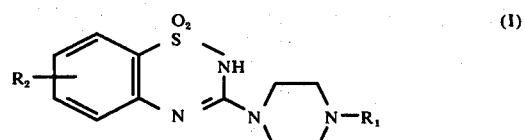

wherein $R_1$ represents a hydrogen atom or a lower alkyl group, and $R_2$ represents a hydrogen, chlorine or bromine atom or a trifluoromethyl group in 6- or 7-position, or its pharmaceutically acceptable salt.

2. 7-Chloro-3-(4-methyl-1-piperazinyl)-2H-1,2,4-benzothiadiazine 1,1-dioxide, or its pharmaceutically acceptable salt.

3. 3-(4-Methyl-1-piperazinyl)-2H-1,2,4-benzothiadiazine 1,1-dioxide, or its pharmaceutically acceptable salt.

4. A pharmaceutical composition comprising, as an active ingredient, a compound of the formula

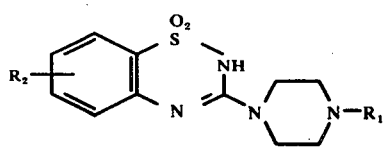

(I)

wherein $R_1$ represents a hydrogen atom or a lower alkyl group, and $R_2$ represents a hydrogen, chlorine or bromine atom or a trifluoromethyl group in the 6- or 7position,
or its pharmaceutically acceptable salt in admixture with a pharmaceutically acceptable carrier.

5. The pharmaceutical composition of claim 4 wherein said compound of formula (I) is 7-chloro-3-(4-methyl-1-piperazinyl)-2H-1,2,4-benzothiadiazine 1,1-dioxide or its pharmaceutically acceptable salt.

6. The pharmaceutical composition of claim 4 wherein said compound of formula (I) is 3-(4-methyl-1-piperazinyl)-2H-1,2,4-benzothiadiazine 1,1-dioxide or its pharmaceutically acceptable salt.

7. The pharmaceutical composition of claim 4 in a form suitable for oral administration.

8. A method for treating hypertension which comprises administering to a patient suffering from hypertension a pharmaceutically effective amount of a compound of the formula

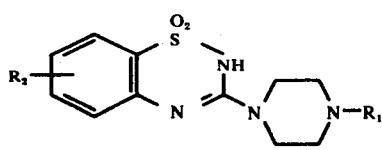

(I)

wherein $R_1$ represents a hydrogen atom or a lower alkyl group, and $R_2$ represents a hydrogen, bromine or chlorine atom or a trifluoromethyl group at the 6- or 7-position,
or its pharmaceutically acceptable salt.

9. The method of claim 8 wherein said patient is a human and said pharmaceutically effective amount is 1 to 10 mg/kg/day and said compound is administered by an oral route.

10. The method of claim 9 wherein said compound is 7-chloro-3-(4-methyl-1-piperazinyl)-2H-1,2,4-benzothiadiazine 1,1-dioxide or its pharmaceutically acceptable salt.

11. The method of claim 9 wherein said compound is 3-(4-methyl-1-piperazinyl)-2H-1,2,4-benzothiadiazine 1,1-dioxide, or its pharmaceutically acceptable salt.

* * * * *